United States Patent [19]

Osuna Carillo de Albornoz et al.

[11] Patent Number: 4,844,900

[45] Date of Patent: Jul. 4, 1989

[54] THERAPEUTIC AGENTS IN THE FORM OF SUBMICROSCOPIC PARTICLES AGAINST LEISHMANIASIS AND PHARMACEUTICAL COMPOSITIONS CONTAINING THEM

[75] Inventors: Antonio Osuna Carillo de Albornoz; Santiago Castanys, both of Granada, Spain

[73] Assignee: N.V. Sopar S.A., Brussels, Belgium

[21] Appl. No.: 105,257

[22] Filed: Oct. 7, 1987

[30] Foreign Application Priority Data

Oct. 8, 1986 [FR] France ................................ 86 13999

[51] Int. Cl.$^4$ .............................................. A61K 31/78
[52] U.S. Cl. ................................................................ 424/81
[58] Field of Search ............................................. 424/81

[56] References Cited

U.S. PATENT DOCUMENTS 4,186,183  1/1980  Steck et al. .......................... 424/450
4,489,055  12/1984  Couvreur et al. ................... 424/425

FOREIGN PATENT DOCUMENTS 0007895  2/1980  European Pat. Off. .
0064967  11/1982  European Pat. Off. .

OTHER PUBLICATIONS

Chemical Abstracts, vol. 98, No. 21, May 23, 1983, p. 364, No. 185458v, Columbus, Ohio, US; J. Kreuter.
Chemical Abstracts, vol. 104, No. 20, May 19, 1986, p. 384, No. 174575x, Columbus, Ohio, US; M. S. El-Samaligy et al.
Chemical Abstracts, vol. 105, No. 21, Nov. 24, 1986, p. 404, No. 187450y, Columbus, Ohio, US; L. Golightly et al.
Chemical Abstracts, vol. 72, No. 5, Feb. 2, 1970, p. 174, No. 20279n, Columbus, Ohio, US; L. M. Gordeeva et al.
Chemical Abstracts, vol. 73, 1970, p. 226, No. 129274d, Columbus, Ohio, U.S.; P. J. Van Dijck et al.

*Primary Examiner*—Joseph L. Schofer
*Assistant Examiner*—Peter F. Kulkosky
*Attorney, Agent, or Firm*—Cushman, Darby & Cushman

[57] ABSTRACT

The invention relates to new therapeutic agents against Leishmaniasis.

These therapeutic agents consist of submicroscopic particles whose diameter is less than 500 nanometers, the particles being obtained by the micellar polymerization of an alkyl cyanoacrylate in which the alkyl chain contains from 1 to 12 carbon atoms.

The therapeutic agents according to the invention may be administered parenterally.

11 Claims, No Drawings

THERAPEUTIC AGENTS IN THE FORM OF SUBMICROSCOPIC PARTICLES AGAINST LEISHMANIASIS AND PHARMACEUTICAL COMPOSITIONS CONTAINING THEM

BACKGROUND OF THE INVENTION

1. Field of the Invention

The present invention relates to new therapeutic agents against Leishmaniasis, and to pharmaceutical compositions containing them.

The term Leishmaniasis denotes a group of conditions which are caused in man and other mammals by different species of parasites of the genu Leishmania. The most important species are *Leishmania tropica, Leishmania aethiopica, Leishmania mexicana, Leishmania braziliensis* and *Leishmania donovani* [F. Wunderlich and E. Schurr, Biologie in unserer Zeit 14 (1984), 111–120].

The known pharmaceutical agents which are universally administered against this condition, namely, in particular, dehydroemetine and amphotericin B, exert, apart from the desired activity, very toxic and adverse side effects.

The object of the invention is consequently to obtain new therapeutic agents against Leishmaniasis which are less toxic at equal activity than the traditional active principles, or which have higher activity for approximately equal toxicity.

2. Description of the prior art

From the documents EP-B-0,007,895 and EP-B-0,064,967, submicroscopic particles that are obtained by the micellar polymerization of alkyl cyanoacrylates, and which contain a biologically active substance in absorbed or adsorbed form, are known.

As stated in these documents, these submicroscopic polymeric particles which contain a biologically active substance may be used for the treatment of many diseases, and in particular certain types of cancer. These particles containing a biologically active substance may be administered parenterally and afford, in particular, the advantage of being biodegradable and of exerting a prolonged therapeutic action which is more effective than that which can be obtained by the administration of the biologically active substance alone (not contained in particles). In addition, the toxicity of the particles containing the substance is lower than that of the biologically active substance alone.

SUMMARY OF THE INVENTION

It has been discovered, surprisingly, that the submicroscopic particles prepared by the polymerization of cyanoacrylic acid derivatives, according to the processes described in the documents EP-B-0,007,895 and EP-B-0,064,967, are active against the known forms of Leishmaniasis, this being the case even when these particles do not contain any pharmaceutical agent known for its activity against Leishmaniasis. It has been found that, when administered parenterally, these particles, free from other substances, exert a very marked therapeutic effect against Leishmaniasis resembling that of the drugs known to be active against this disease, while not having the toxicity of these drugs.

Since it is known, following many investigations, that these submicroscopic particles based on polymers of alkyl cyanoacrylates are only slightly toxic, or are nontoxic, at least as regards the quantities administered for therapeutic purposes, these pure submicroscopic particles free from other active principles are suitable as effective therapeutic agents against Leishmaniasis.

It has been found, in addition, that the simultaneous administration of certain chemotherapeutic agents, known for their activity against Leishmaniasis, and submicroscopic particles based on polymers of alkyl cyanoacrylate enables a therapeutic effect to be attained which is superior to that which is obtained with the said submicroscopic particles alone or with the said chemotherapeutic agents alone.

When the said chemotherapeutic agents are used simultaneously with the said submicroscopic particles, the toxicity and the adverse side effects of the chemotherapeutic agents are markedly reduced when the latter are in adsorbed or absorbed form in the submicroscopic particles.

DETAILED DESCRIPTION OF THE INVENTION

The subject of the invention is hence a therapeutic agent against Leishmaniasis which consists of submicroscopic particles whose diameter is less than 500 nanometers, the particles being obtained by the micellar polymerization of at least one alkyl cyanoacrylate.

More specifically, submicroscopic particles based on polymeric alkyl cyanoacrylate in which the linear or branched alkyl chain comprises 1 to 12 carbon atoms, and especially 4 to 7 carbon atoms, are employed.

According to one embodiment, the submicroscopic particles are obtained by the copolymerization of at least two different alkyl cyanoacrylates.

In particular, these particles may be obtained by the micellar polymerization of isobutyl cyanoacrylate (2-methylpropyl cyanoacrylate) and/or isohexyl cyanoacrylate (2-ethylbutyl cyanoacrylate).

The submicroscopic particles which constitute the therapeutic agents according to the invention may be prepared according to the processes described in the documents EP-B-0,007,895 or EP-B-0,064,967, and consist of the abovementioned polymers formed by polymerization or copolymerization.

It is surprising that these pure polymeric submicroscopic particles, free from other active principles, exert a very effective therapeutic action against Leishmaniasis, this action resembling that of the drugs known to be active against this disease.

This therapeutic action can, if desired, be made still more effective is use is made of polymeric submicroscopic particles containing at least one substance known to be active against Leishmaniasis.

In particular, use may thus be made of particles charged with dehydroemetine and/or amphotericine B.

The therapeutic agents according to the invention contain the submicroscopic particles, containing or not containing another antiparasitic substance, in the form of a suspension or colloidal solution in physiologically compatible solutions, or alternatively are dry powders which are brought into suspension or colloidal solution before administration in physiological compatible solutions, for example sodium chloride or dextrose solution.

The subject of the invention is also pharmaceutical compositions to be administered parenterally and containing at least one therapeutic agent according to the invention in combination with a suitable vehicle.

The subject of the invention is also such pharmaceutical compositions containing, in addition, amphotericine B.

EXAMPLE 1

The activity of therapeutic agents according to the invention was tested on white rate (average weight: 340 g) which were inoculated with a single dose of $50 \times 10^6$ causal agents of the condition (Leishmania donovani).

The test animals were treated by means of various therapeutic agents 30 days after the inoculation.

Each treatment consisted of three intracardiac injections, each of 1 ml, administered at 7-day intervals, except in the case of dehydroemetine alone which, on account of its high cardiac toxicity, was injected intraperitoneally.

The experimental doses injected (each having a suitable content of active principle):

(a) dehydroemetine in aqueous solution at a concentration of 1.2 mg per ml, (b) submicroscopic particles based on polymerized isohexyl cyanoacrylate not containing any other active substance, in aqueous suspension at a concentration of 24 mg per ml, (c) submicroscopic particles based on polymerized hexyl cyanoacrylate containing 5% of dehydroemetine (each ml of the suspension contains 24 mg of submicroscopic particles and 1.2 mg of dehydroemetine).

After the treatment, the causal agents present in the spleen were determined and compared with those found in similarly inoculated but untreated animals

| Treatment | Results | |
|---|---|---|
| | Causal agents of the condition, per gram of spleen | Reduction in the causal agents (%) |
| — | $36.015 \times 10^6$ | |
| a | $4.870 \times 10^6$ | 86.5 |
| b | $6.550 \times 10^6$ | 81.8 |
| c | $0.585 \times 10^6$ | 98.4 |

EXAMPLE 2

Other rats, of average weight 300 g, received a single dose of $12 \times 10^6$ causal agents of the condition.

The therapeutic agents were injected intravenously; the treatment began 30 days after the inoculation and consisted of 3 injections of 0.5 ml, administered at 7-day intervals.

Experimental doses injected:

(a') dehydroemetine in aqueous solution, in the proportion of 1.75 mg per kg of rat, (b') submicroscopic particles based on polymerized isohexyl cyanoacrylate, in aqueous suspension, in the proportion of 35 mg per kg of rat, (c') submicroscopic particles based on polymerized isohexyl cyanoacrylate containing dehydroemetine (in the proportion of 1.75 mg of dehydroemetine and 35 mg of submicroscopic particles per kg of rat).

After treatment, the causal agents present per 100 normal nucleated spleen cells were determined and compared with those found in untreated controls.

| Treatment | Results | |
|---|---|---|
| | Causal agents of the condition, per 100 spleen cells | Reduction in the causal agents (%) |
| — | 28 | |
| a' | 16 | 42.86 |
| b' | 12 | 57.1 |
| c' | 12 | 57.1 |

EXAMPLE 3

The activity of therapeutic agents according to the invention was tested in a similar manner to that of Example 2, but amphotericin B was used instead of dehydroemetine as the biologically active substance.

Rats of average weight 300 g received a single dose of $12 \times 10^6$ causal agents of the condition.

The therapeutic agents were injected intravenously; the treatment was begun 30 days after the inoculation and consisted of 3 injections of 1 ml, administered at 7-day intervals.

Experimental doses administered:

(a'') amphotericin B in aqueous solution, in the proportion of 2.5 mg per kg of rat, (b'') submicroscopic particles based on polymerized isohexyl cyanoacrylate, in aqueous suspension, in the proportion of 35 mg per kg of rat, (c'') submicroscopic particles based on polymerized isohexyl cyanoacrylate containing amphotericin B (in the proportion of 2.5 mg of amphotericin B and 35 mg of submicroscopic particles per kg of rat).

After treatment, the causal agents present per gram of spleen were determined and compared with those found in controls.

| Treatment | Results | |
|---|---|---|
| | Causal agents of the condition, per gram spleen cells | Reduction in the causal agents (%) |
| — | $11 \times 10^6$ | |
| a'' | $2.8 \times 10^6$ | 74.5 |
| b'' | $4.8 \times 10^6$ | 56.5 |
| c'' | $2 \times 10^6$ | 81.8 |

We claim:

1. A therapeutic composition for the treatment of Leishmaniasis that is relatively nontoxic in therapeutic quantities, consisting essentially of submicroscopic particles whose diameter is less than 500 nanometers as the sole essential therapeutic agent, the particles being obtained by micellar polymerization of at least one alkyl cyanoacrylate in which the linear or branched alkyl chain contains from 1 to 12 carbon atoms and wherein the particles are combined only with a nontoxic pharmaceutically acceptable vehicle, wherein the particles are the sole treating agent and these are free of substances known to be active against Leishmaniasis.

2. A therapeutic composition for the treatment of Leishmaniasis that is relatively nontoxic in therapeutic quantities, comprising submicroscopic particles whose diameter is less than 500 nanometers as the sole essential therapeutic agent, the particles being obtained by polymerization of at least one alkyl cyanoacrylate in which the linear or branched alkyl chain contains from 5 to 12 carbon atoms wherein the particles are the sole treating agent and these are free of substances known to be active against Leishmaniasis.

3. The therapeutic composition as claimed in claim 2, further comprising submicroscopic particles obtained by the copolymerization of at least two different alkyl cyanoacrylates in which the linear or branched alkyl chain contains from 1 to 12 carbon atoms.

4. The therapeutic composition as claimed in claim 2, wherein the submicroscopic particles are obtained by the polymerization of 2-methylpropyl cyanoacrylate.

5. The therapeutic composition as claimed in claim 2, wherein the submicroscopic particles are obtained by the polymerization of 2-ethylbutyl cyanoacrylate.

6. A pharmaceutical composition that is relatively nontoxic in therapeutic quantities in a form suitable to be administered parentally for the treatment of Leishmaniasis, comprising at least one therapeutic agent consisting essentially of submicroscopic particles whose diameter is less than 500 nanometers, the particles being obtained by micellar polymerization of at least one alkyl cyanoacrylate in which the linear or branched alkyl chain contains from 1 to 12 carbon atoms, in combination with and combined only with a suitable nontoxic vehicle, wherein the particles are the sole treating agent and these are free of substances known to be active against Leishmaniasis.

7. The pharmaceutical composition as claimed in claim 6, in which the submicroscopic particles are obtained by polymerization of at least one alkyl cyanoacrylate in which the linear or branched alkyl chain contains from 5 to 12 carbon atoms.

8. The pharmaceutical composition as claimed in claim 7, in which the submicroscopic particles are obtained by the polymerization of 2-methylpropyl cyanoacrylate.

9. The pharmaceutical composition as claimed in claim 7, in which the submicroscopic particles are obtained by the polymerization of 2-ethylbutyl cyanoacrylate.

10. A method for treating Leishmaniasis, which comprises administering to a host in need of such treatment, an effective amount of submicroscopic particles having a diameter of less than 500 nanometers, the particles being obtained by micellar polymerization of at least one alkyl cyanoacrylate in which the linear or branched chain contains from 1 to 12 carbon atoms, wherein the particles are the sole treating agent and these are free of substances known to be active against Leishmaniasis.

11. A method for treating Leishmaniasis as claimed in claim 10, wherein the particles are parentally administered to the host.

* * * * *